US00PP33927P2

(12) United States Plant Patent
van Langen

(10) Patent No.: US PP33,927 P2
(45) Date of Patent: Feb. 1, 2022

(54) ***ECHEVERIA* PLANT NAMED 'AMIECH2107'**

(50) Latin Name: ***Echeveria agavoides* Lem. x *Echeveria purpusorum* A. Berger.**
Varietal Denomination: AMIECH2107

(71) Applicant: Novoami B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 17/300,643

(22) Filed: Sep. 8, 2021

(30) Foreign Application Priority Data

Apr. 13, 2021 (QZ) ..... PBR 2021/1010

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* hybrid plant named 'AMIECH2107' which is characterized by an abundance of moderately glossy, glaucescent foliage that is tightly held in a compact basal rosette, green juvenile foliage at the center of the rosette, yellow-green to greyed-green mature foliage that is suffused with greyed-red at and near the apex on the adaxial surface, mature foliage with an abaxial surface that is heavily suffused with greyed-red, and the stability of these characteristics from generation to generation.

4 Drawing Sheets

Latin name of the genus and species: The Latin name of the genus and species of the novel variety disclosed herein is *Echeveria agavoides* Lem. x *Echeveria purpusorum* A. Berger.

Variety denomination: The inventive variety of *Echeveria* hybrid disclosed herein has been given the variety denomination 'AMIECH2107'.

CROSS REFERENCE TO RELATED APPLICATIONS

This application claims priority to the Community Plant Variety Rights application number 2021/1010, filed Apr. 13, 2021, which is herein incorporated by reference.

BACKGROUND OF THE INVENTION

Parentage: 'AMIECH2107' is an interspecific hybrid seedling selection resulting from the controlled pollination of an unnamed *Echeveria agavoides* plant (not patented), the seed parent, with an unnamed *Echeveria purpusorum* plant (not patented), the pollen parent. The crossing was made by the inventor in the spring of 2018 at a commercial greenhouse in Heerhugowaard, the Netherlands. In summer of 2019, one seedling was observed which exhibited unique growth and foliage characteristics. The seedling was isolated for further evaluation in order to confirm the distinctness and stability of the characteristics first observed. Upon confirmation of distinctness and stability, 'AMIECH2107' was selected for commercialization.

Asexual Reproduction: Asexual reproduction of the new cultivar 'AMIECH2107', by way of rooting leaf cuttings, was first initiated in the autumn of 2019 at the inventor's commercial greenhouse in Heerhugowaard, the Netherlands. Through three subsequent generations, the unique features of this cultivar have proven to be stable and true to type.

SUMMARY OF THE INVENTION

The cultivar 'AMIECH2107' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2107'. These characteristics in combination distinguish 'AMIECH2107' as a new and distinct *Echeveria* hybrid cultivar:

1. 'AMIECH2107' exhibits a flattened globular plant profile with foliage tightly arranged in an unbranched, compact basal rosette; and
2. 'AMIECH2107' exhibits slightly concave, obovate foliage with a bluntly apiculate apex; and
3. 'AMIECH2107' exhibits moderately glossy, glaucescent foliage; and
4. 'AMIECH2107' exhibits green juvenile foliage at the center of the rosette; and
5. 'AMIECH2107' exhibits yellow-green to greyed-green mature foliage that is suffused with greyed-red at and near the apex on the adaxial surface and an abaxial surface that is heavily suffused with greyed-red.

BOTANICAL DESCRIPTION OF THE PLANT

Figure 1:
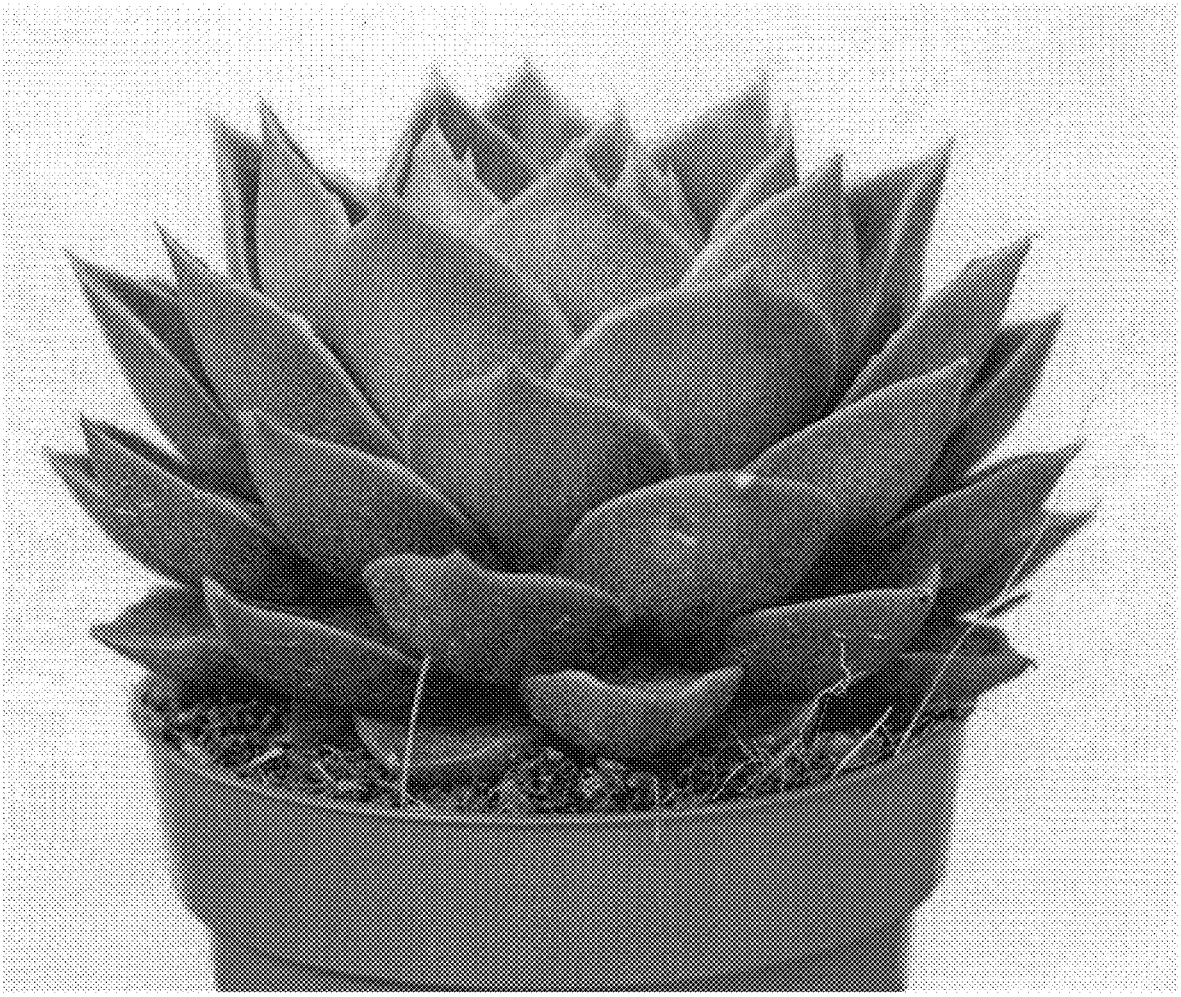
FIG. 1 illustrates, as nearly true as it is reasonably possible to make the same in color photographs of this type, an exemplary plant of 'AMIECH2107' grown in a commercial greenhouse in Heerhugowaard, the Netherlands. This plant is approximately 12 month-old, shown planted in an 8.5 cm container.
Figure 2:
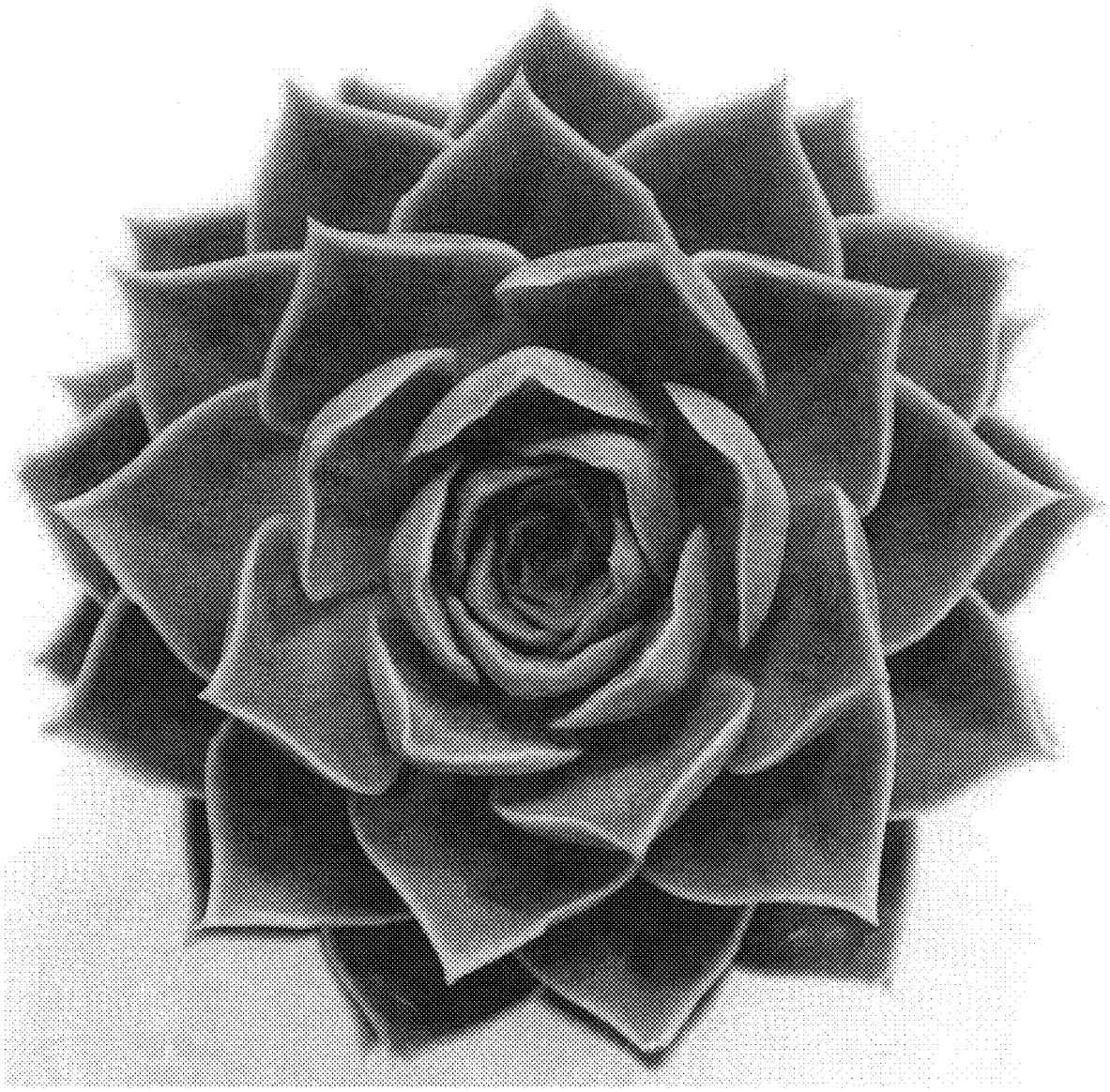
FIG. 2 illustrates, as nearly true as it is reasonably possible to make the same in color photographs of this type, the typical foliage arrangement of 'AMIECH2107.
Figure 3:
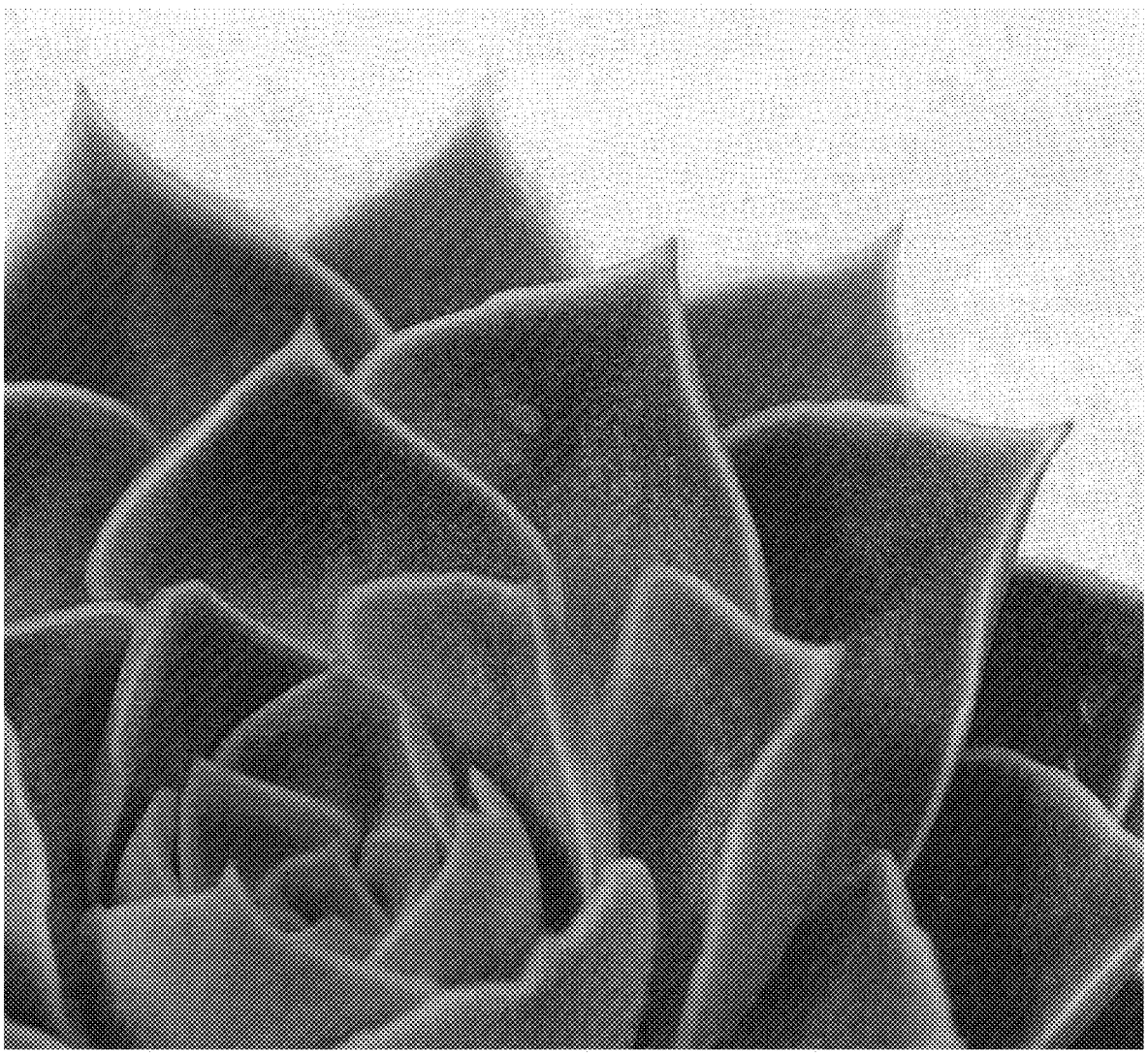
FIG. 3 illustrates, as nearly true as it is reasonably possible to make the same in color photographs of this type, the adaxial surface of the mature foliage 'AMIECH2107'.
Figure 4:
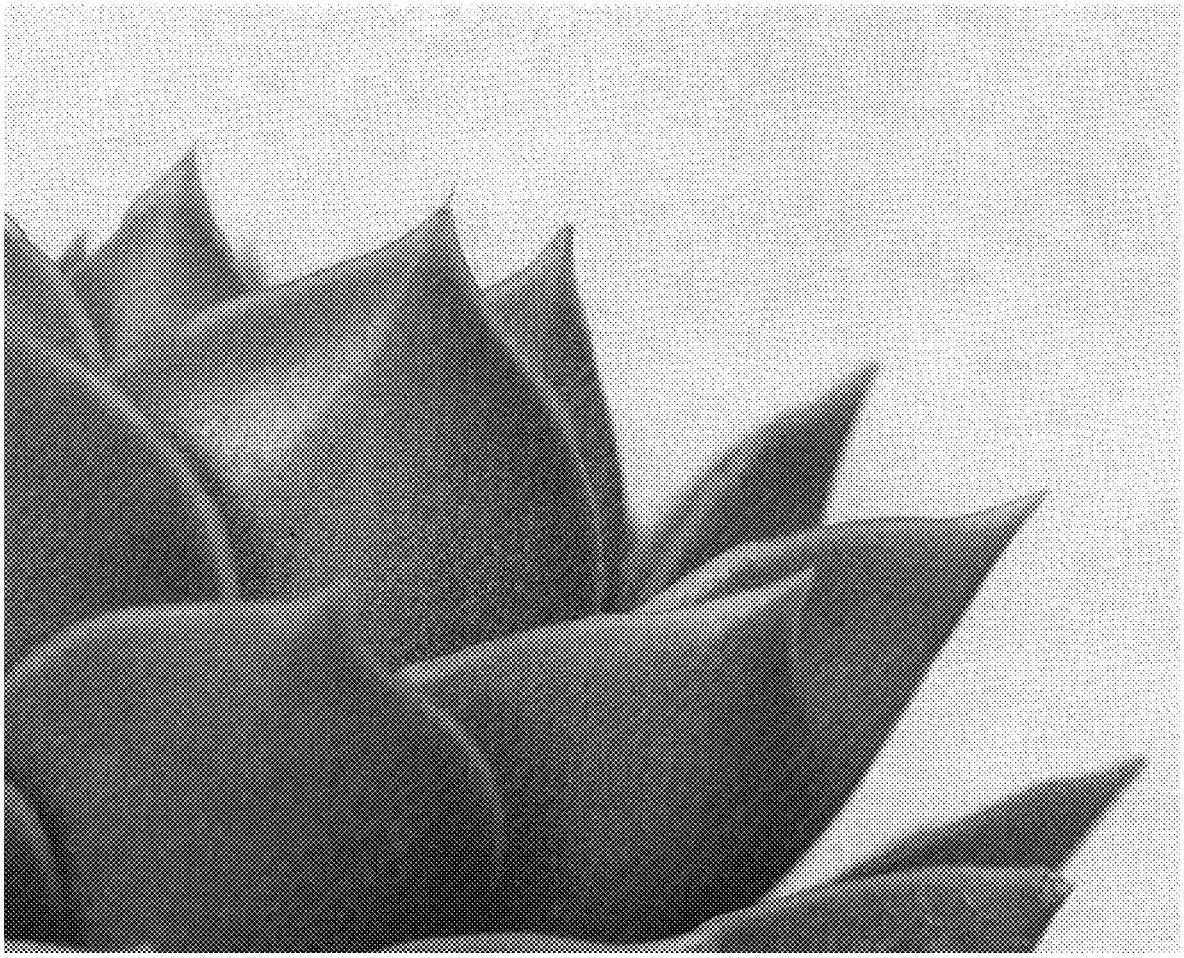
FIG. 4 illustrates, as nearly true as it is reasonably possible to make the same in color photographs of this type, the abaxial surface of the mature foliage 'AMIECH2107'.

The following observations and measurements made in June of 2021 describe averages from a sample set of six specimens of 12 month-old 'AMIECH2107' plants grown in 8.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2107' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'AMIECH2107' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—7.1 cm.

*Plant spread*.—Average of 10.9 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 62 leaves per rosette.

*Shape*.—Obovate.

*Dimensions*.—5.1 cm long, 2.8 cm wide, and 0.7 cm thick, on average.

*Aspect*.—Slightly concave.

*Attitude*.—Juvenile foliage at the center of the rosette is held upright; foliage becomes progressively more relaxed towards the outer whorls of mature foliage.

*Apex*.—Bluntly apiculate.

*Base*.—Cuneate.

*Margin*.—Entire; not undulate.

*Pubescence, texture and luster of the adaxial surface*.—Glabrous, smooth, and glaucescent.

*Pubescence, texture and luster of the abaxial surface*.—Glabrous, smooth, and glaucescent.

*Luster of the adaxial surface*.—Moderately glossy.

*Luster of the abaxial surface*.—Moderately glossy.

*Color*.—Juvenile foliage, adaxial surface — Green, nearest to a mixture of RHS 138A and N138B, and fading to yellow-green towards the base, nearest to RHS 145C; tipped and narrowly margined yellow-green, nearest to RHS 146D. The epicuticular glaucous wax covering the leaf surface is greyed-green, nearest to RHS 192A. Juvenile foliage, abaxial surface — A mixture of green and greyed-green, nearest to RHS 138B and 191B, and fading to a lighter shade of greyed-green towards the base, nearest to RHS 196B; tipped and narrowly margined with a translucent yellow-green, nearest to RHS 146D. The epicuticular glaucous wax covering the leaf surface is greyed-purple, nearest to RHS N187D. Mature foliage, adaxial surface — A mixture of yellow-green and greyed-green, nearest to RHS 147A and 189A yet closest to 147A; fading to yellow-green towards the base, nearest to a combination of RHS N148A and N148B; lightly to moderately suffused with greyed-red towards the apex, nearest to RHS 181C; tipped and narrowly margined with a translucent yellow-green, nearest to RHS 152D. The epicuticular glaucous wax covering the leaf surface is greyed-green, nearest to RHS 192A. Mature foliage, abaxial surface — Greyed-green, nearest to RHS 197A, and suffused with greyed-red, nearest to RHS 181C; fading to a lighter shade of greyed-green towards the base, nearest to RHS 146A; margined with a mixture of yellow-green and grey-brown, nearest to RHS 152D and 199C; tipped with greyed-orange, nearest to RHS 177D. The epicuticular glaucous wax covering the leaf surface is greyed-purple, nearest to RHS N187D. Venation, adaxial surface — No visible venation. Venation, abaxial surface — No visible venation.

*Petiole*.—No petiole; leaves are sessile.

Inflorescence: No flowering has been observed to date.

Comparisons With the Parent Plants and Closest Known Comparator

Plants of the new cultivar 'AMIECH2107' differ from the seed parent, an unnamed *Echeveria purpusorum* plant (not patented), in the following characteristics described in Table 1 below.

TABLE 1

| Characteristic | 'AMIECH2107' | The seed parent. |
|---|---|---|
| Plant size. | Larger than the seed parent. | Smaller than 'AMIECH2107'. |
| Foliage thickness. | Thinner than the seed parent. | Thicker than 'AMIECH2107'. |
| General coloration of the mature foliage. | Green; adaxial surface is moderately suffused with greyed-red towards the apex; the abaxial surface is heavily suffused with greyed-red. | Green. |

Plants of the new cultivar 'AMIECH2107' differ from the pollen parent, an unnamed *Echeveria agavoides* plant (not patented), in the following characteristics described in Table 2 below.

TABLE 2

| Characteristic | 'AMIECH2107' | The pollen parent. |
|---|---|---|
| Foliage length. | Shorter than the pollen parent. | Longer than 'AMIECH2107'. |
| General coloration of the mature foliage. | Green; adaxial surface is moderately suffused with greyed-red towards the apex; the abaxial surface is heavily suffused with greyed-red. | Green. |

Comparisons With the Closest Known Comparator

Plants of the new cultivar 'AMIECH2107' differ from the closest known commercial comparator, *Echeveria* hybrid 'Mensa' (Community Plant Variety Rights application number 30403), in the following characteristics described in Table 3 below.

TABLE 3

| Characteristic | 'AMIECH2107' | 'Mensa' |
|---|---|---|
| Growth habit. | More compact than 'Mensa'. | Less compact than 'AMIECH2107'. |
| General coloration of the mature foliage. | Green; adaxial surface is moderately suffused with greyed-red towards the apex; the abaxial surface is heavily suffused with greyed-red. | Greyed-green. |

That which is claimed is:

1. A new and distinct variety of *Echeveria agavoides* Lem. x *Echeveria purpusorum* A. Berger plant named 'AMIECH2107', substantially as described and illustrated herein.

* * * * *